(12) United States Patent
Venkatesha et al.

(10) Patent No.: US 11,993,386 B2
(45) Date of Patent: May 28, 2024

(54) SMART SYSTEMS AND METHODS FOR AUTOMATIC DEPLOYMENT OF AN EJECTION SYSTEM

(71) Applicant: AMI INDUSTRIES, INC., Colorado Springs, CO (US)

(72) Inventors: Harish Venkatesha, Karnataka State (IN); Ashish Vijay, Bikaner (IN); Ajay Kumar Mishra, Bangalore (IN); Glen Shaw, Colorado Springs, CO (US); Dustin J. Wimmer, Colorado Springs, CO (US)

(73) Assignee: AMI INDUSTRIES, INC., Colorado Springs, CO (US)

( * ) Notice: Subject to any disclaimer, the term of this patent is extended or adjusted under 35 U.S.C. 154(b) by 266 days.

(21) Appl. No.: 17/497,624

(22) Filed: Oct. 8, 2021

(65) Prior Publication Data

US 2022/0127008 A1 Apr. 28, 2022

(30) Foreign Application Priority Data

Oct. 23, 2020 (IN) .............................. 202041046347

(51) Int. Cl.
*B64D 25/10* (2006.01)
*A61B 5/18* (2006.01)
(Continued)

(52) U.S. Cl.
CPC ................ *B64D 25/10* (2013.01); *A61B 5/18* (2013.01); *B64D 47/02* (2013.01); *B64D 2045/0085* (2013.01)

(58) Field of Classification Search
CPC ........ B64D 25/00; B64D 25/08; B64D 25/10; B64D 47/02; B64D 2045/0085; A61B 5/18
See application file for complete search history.

(56) References Cited

U.S. PATENT DOCUMENTS 6,507,776 B1 * 1/2003 Fox, III ............... G05D 1/0055
 244/76 R
7,228,169 B2 6/2007 Viertio-Oja et al.
(Continued)

FOREIGN PATENT DOCUMENTS

| CN | 107804468 A | 3/2018 |
| EP | 1395176 | 3/2004 |
| EP | 2789293 | 12/2013 |

OTHER PUBLICATIONS

Noirhomme, et al., "Consciousness and Unconsciousness: An EEG Perspective", Clinical EEG and Neuroscience, Official Journal of the EEG and Clinical Neuroscience Society (ENCS), sagepub.com/journalsPermissions.nav, DOI: 10.1177/1550059413519518, (2014), vol. 45(I), pp. 4-5.

(Continued)

*Primary Examiner* — Michael H Wang
(74) *Attorney, Agent, or Firm* — SNELL & WILMER L.L.P.

(57) ABSTRACT

An ejection system may comprise an ejection seat and a smart deployment system configured to initiate a deployment of the ejection seat. The smart deployment system may comprise a pilot health monitoring system including a plurality of sensors configured to detect a plurality of physiological conditions, and a controller configured to make ejection system decisions based on a pilot health signal received from the pilot health monitoring system and an aircraft health signal output from an aircraft health monitoring system.

20 Claims, 4 Drawing Sheets

(51) Int. Cl.
  *B64D 47/02* (2006.01)
  *B64D 45/00* (2006.01)

(56) References Cited

U.S. PATENT DOCUMENTS

| | | | |
|---|---|---|---|
| 7,271,713 | B2 | 9/2007 | Ayoub et al. |
| 7,774,052 | B2 | 8/2010 | Burton et al. |
| 8,164,464 | B2* | 4/2012 | Matos ............... A62B 99/00 |
| | | | 702/182 |
| 8,289,172 | B2* | 10/2012 | Matos ............... A62B 99/00 |
| | | | 340/576 |
| 8,761,965 | B2* | 6/2014 | Righi ............ B64D 45/0031 |
| | | | 701/8 |
| 9,102,417 | B1* | 8/2015 | Young ............... A61B 5/6814 |
| 9,579,060 | B1* | 2/2017 | Lisy ...................... A61B 5/16 |
| 9,919,712 | B1* | 3/2018 | Doyen ............ A61B 5/14542 |
| 2003/0034902 | A1* | 2/2003 | Dickau ............. G05D 1/0061 |
| | | | 340/963 |
| 2005/0230545 | A1* | 10/2005 | Ayoub ................. B64D 25/10 |
| | | | 244/122 A |
| 2016/0071393 | A1* | 3/2016 | Kaplan ................ A61B 5/162 |
| | | | 340/539.12 |
| 2019/0369615 | A1* | 12/2019 | Martinez Jara ........ B64D 43/00 |
| 2021/0004617 | A1* | 1/2021 | Gouraud ............. G06V 20/597 |
| 2021/0290102 | A1* | 9/2021 | Burwinkel ............. A61B 5/162 |
| 2022/0405518 | A1* | 12/2022 | Atassi ................... G06V 40/20 |

OTHER PUBLICATIONS

Bureau of Air Safety Invenstigtion, Dept. of Transport Communications, "The Possibility of G-Induced Loss of Consciousness (G-LOC) During Aerobatics in a Light Aircraft", Feb. 1988 (1988), Research Report 872-1017, Canberra, Australia, pp. 1-10.

Dias, et al., "Wearable Health Devices—Vital Sign Monitoring, Systems and Technologies", MDPI Journal, Sensors, www.mdpi.com/journal/sensors, vol. 18, 2414; doi:10.3390/s18082414, Published: Jul. 25, 2018 (2018), pp. 1-28.

* cited by examiner

SMART SYSTEMS AND METHODS FOR AUTOMATIC DEPLOYMENT OF AN EJECTION SYSTEM

CROSS-REFERENCE TO RELATED APPLICATIONS

This application claims priority to, and the benefit of, India Patent Application No. 202041046347, filed Oct. 23, 2020 and titled "SMART SYSTEMS AND METHODS FOR AUTOMATIC DEPLOYMENT OF AN EJECTION SYSTEM," which is incorporated by reference herein in its entirety for all purposes.

FIELD

The present disclosure relates to ejection systems for aircraft and, more particularly, to smart systems and methods for automatic deployment of the ejection system based on data collected from the ejection seat occupant and aircraft health monitoring system.

BACKGROUND

Certain aircraft may include ejection systems designed to eject a member of the flight crew from the aircraft in certain situations. These ejection systems typically include an ejection seat in which the member of the flight crew is located during flight. Current ejection systems depend on the seat occupant to manually activate ejection sequence, for example, by pulling a handle. If the seat occupant is incapacitated, he/she may not be able to pull the ejection handle or otherwise initiate the ejection sequence.

SUMMARY

Disclosed herein is a smart deployment system for an ejection system. In accordance with various embodiments, the smart deployment system may comprise a pilot health monitoring system including a plurality of sensors configured to detect a plurality of physiological conditions, and an aircraft health monitoring system configured to monitor one or more parameters of an aircraft. A controller may be operationally coupled to the pilot health monitoring system and the aircraft health monitoring system. A tangible, non-transitory memory may be configured to communicate with the controller. The tangible, non-transitory memory may have instructions stored thereon that, in response to execution by the controller, cause the controller to perform operations, which may comprise: receiving, by the controller, a pilot health signal from the pilot health monitoring system; receiving, by the controller, an aircraft health signal from the aircraft health monitoring system; determining, by the controller, at least one of a consciousness or an awareness of an occupant based on the pilot health signal; and determining, by the controller, whether to initiate an ejection sequence based on the at least one of the consciousness or the awareness of the occupant and the aircraft health signal.

In various embodiments, the operations may further comprise detecting, by the controller, if there is an impending danger to the aircraft based on the aircraft health signal. In various embodiments, the operations may further comprise: calculating, by the controller, an estimated time for when the impending danger will occur, in response to the controller detecting the impending danger to the aircraft; and comparing, by the controller, the estimated time for when the impending danger to the aircraft will occur to a predetermined threshold time.

In various embodiments, the operations may further comprise determining, by the controller, if the estimated time for when the impending danger will occur is less than the predetermined threshold time.

In various embodiments, the controller may be configured to send an ejection command configured to initiate the ejection sequence in response to the controller determining that the estimated time for when the impending danger will occur is less than the predetermined threshold time.

In various embodiments, the controller may be configured to recognize a pilot override signal, the pilot override signal being configured to prevent the controller from sending the ejection command to the ejection system.

In various embodiments, the controller may be configured to send a command to a pilot warning system in response to the controller determining that the occupant is at least one of conscious or aware and the controller determining that the estimated time for when the impending danger will occur is greater than or equal to the predetermined threshold time.

In various embodiments, the pilot warning system may be configured to output at least one of an audio alert or a visual alert in response to receiving the command from the controller.

In various embodiments, the controller may be configured to send a command to a pilot recovery mechanism in response to the controller determining that the occupant is at least one of unconscious or unaware and the controller determining that the estimated time for when the impending danger will occur is greater than or equal to the predetermined threshold time.

In various embodiments, the pilot recovery mechanism may be configured to output at least one of an auditory stimuli, a flow of cool air, a flash of light, a vibration, or an electric shock in response to receiving the command from the controller.

In various embodiments, the plurality of sensors may include a first sensor configured to measure electrical brain activity, a second sensor configured to detect eye movement, and a third sensor configured to detect at least one of a heart rate, a blood pressure, or an oxygen level.

A method for controlling deployment of an ejection system for an aircraft is also disclosed herein. In accordance with various embodiments, the method may comprise: receiving, by a controller, a pilot health signal from a pilot health monitoring system; receiving, by the controller, an aircraft health signal from an aircraft health monitoring system; determining, by the controller, at least one of a consciousness or an awareness of an occupant based on the pilot health signal; and determining, by the controller, whether to initiate an ejection sequence based on the at least one of the consciousness or the awareness of the occupant and the aircraft health signal.

In various embodiments, the method may further comprise determining, by the controller, whether or not there is an impending danger to the aircraft based on the aircraft health signal. In various embodiments, the method may further comprise: calculating, by the controller, an estimated time for when the impending danger to the aircraft will occur, in response to the controller detecting the impending danger to the aircraft; and comparing, by the controller, the estimated time for when the impending danger to the aircraft will occur to a predetermined threshold time.

In various embodiments, the method may further comprise sending, by the controller, an ejection command to the ejection system, in response to the controller determining that the estimated time for when the impending danger will occur is less than the predetermined threshold time. The ejection command may be configured to initiate the ejection sequence.

In various embodiments, the method may further comprise sending, by the controller a command to a pilot warning system, in response to the controller determining that the occupant is at least one of conscious or aware and the controller determining that the estimated time for when the impending danger will occur is greater than or equal to the predetermined threshold time.

In various embodiments, the method may further comprise sending, by the controller, a command to a pilot recovery mechanism, in response to the controller determining that the occupant is at least one of unconscious or unaware and the controller determining that the estimated time for when the impending danger will occur is greater than or equal to the predetermined threshold time.

In various embodiments, the pilot recovery mechanism may be configured to output at least one of an auditory stimuli, a flow of cool air, a flash of light, a vibration, or an electric shock in response to receiving the command from the controller.

An ejection system is also disclosed herein. In accordance with various embodiments, the ejection system may comprise an ejection seat and a smart deployment system configured to initiate a deployment of the ejection seat. The smart deployment system may comprise a pilot health monitoring system including a plurality of sensors configured to detect a plurality of physiological conditions, and a controller configured to make ejection system decisions based on a pilot health signal received from the pilot health monitoring system and an aircraft health signal output from an aircraft health monitoring system.

In various embodiments, the controller may be configured to determine whether an occupant of the ejection seat is at least one of conscious or aware based on the pilot health signal, and the controller may be configured to determine if there is an imminent danger in based on the aircraft health signal output from the aircraft health monitoring system.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the figures, wherein like numerals denote like elements.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the exemplary embodiments of the disclosure, it should be understood that other embodiments may be realized and that logical changes and adaptations in design and construction may be made in accordance with this disclosure and the teachings herein. Thus, the detailed description herein is presented for purposes of illustration only and not limitation. The steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts but not necessarily to denote the same or different materials.

As used herein, the term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In re Nuijten to fall outside the scope of patentable subject matter under 35 U.S.C. § 101.

Figure 1:
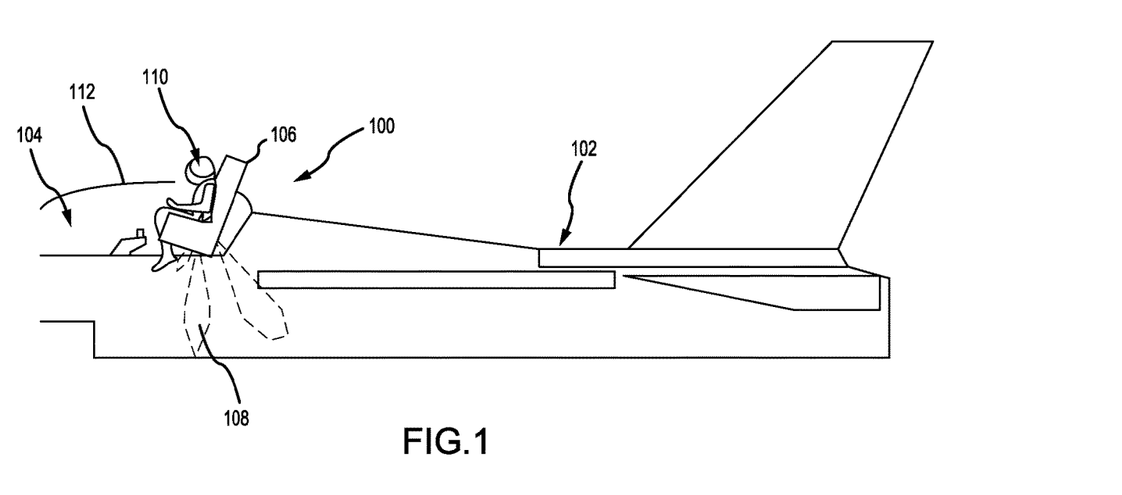
FIG. 1 illustrates an ejection seat being expelled from an aircraft, in accordance with various embodiments.

Referring now to FIG. 1, an aircraft ejection system 100 is shown, in accordance with various embodiments. Aircraft ejection system 100 may be installed in aircraft 102 to safely expel ejection seat 106 and an occupant 110 of ejection seat 106 from cockpit 104 of aircraft 102. Ejection seat 106 may be urged from cockpit 104 by a propulsion system 108. A hatch or canopy 112 may be located over cockpit 104. Canopy 112 may be configured to move relative to the cockpit 104 and/or may be broken during expulsion of ejection seat 106 to allow the members of the flight crew in the cockpit 104 to be ejected from aircraft 102. Aircraft 102 may be a passenger aircraft, a cargo aircraft, a military aircraft, or the like.

Figure 2A:
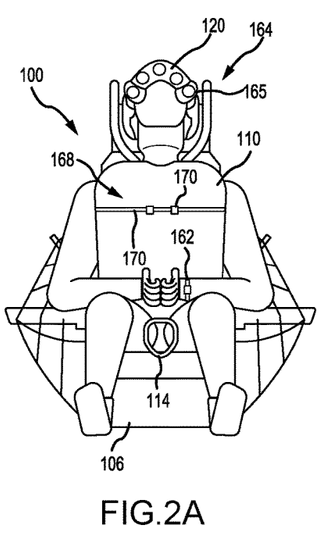
FIGS. 2A and 2B illustrate a front view and a side view, respectively, of various features of an ejection system including an ejection seat and a smart deployment system, in accordance with various embodiments.
Figure 2B:
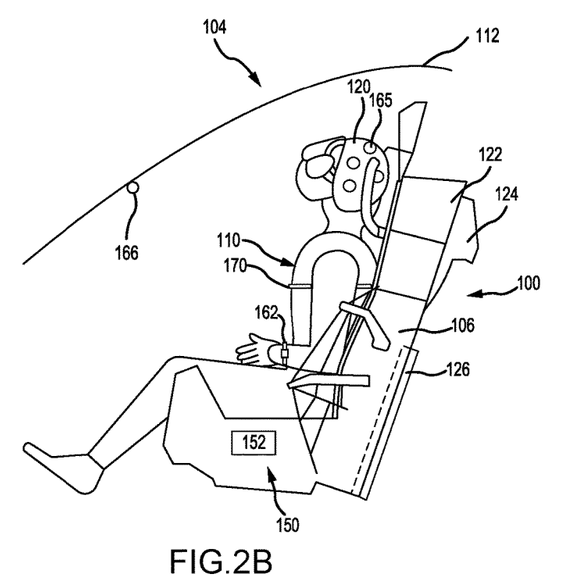

Referring now to FIGS. 2A and 2B, ejection system 100 may be included in the cockpit 104. In particular, ejection system 100 may include ejection seat 106 on which occupant 110 may sit or otherwise rest and a handle 114 configured to deploy ejection system 100. Ejection seat 106 may include various components of ejection system 100 such as a main parachute 122 and a drogue 124. Ejection seat 106 may further include a catapult or rocket 126 that expels ejection seat 106 and occupant 110 from cockpit 104.

Ejection system 100 may be configured to deploy and expel ejection seat 106 from cockpit 104 in response to actuation of handle 114.

Figure 3:
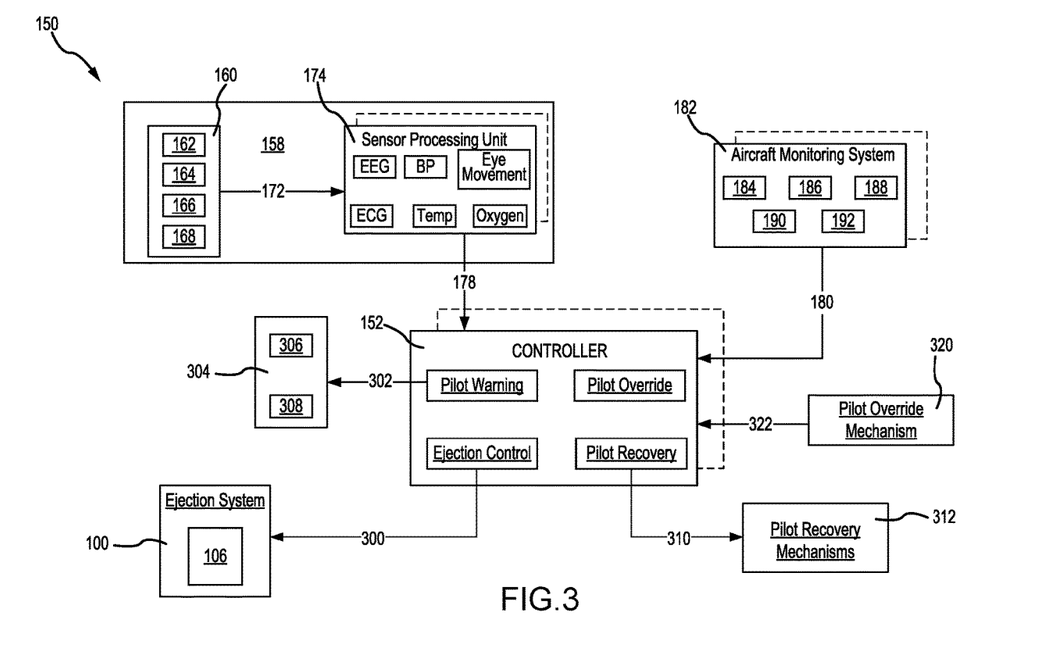
FIG. 3 illustrates a schematic of a smart deployment system for an ejection system, in accordance with various embodiments.

Ejection system 100 may include a smart deployment system 150. FIG. 3 illustrates a schematic of smart deployment system 150. With combined reference to FIG. 2A, FIG. 2B, and FIG. 3, smart deployment system 150 may be configured to initiate deployment of ejection system 100 and expel ejection seat 106 from cockpit 104. Smart deployment system 150 may be configured to monitor a consciousness and/or awareness of occupant 110 using data collected from various sensors operationally coupled to occupant 110. Smart deployment system 150 may also monitor a trajectory and a health of aircraft 102 using various sensors, prognostics and diagnostics modules, operating parameters, and/or other information related to aircraft 102 (e.g., altitude, rate of descent, thrust, fuel level, engine turbine speed, etc.). Smart deployment system 150 may be configured to evaluate a need for ejection of occupant 110 and may automatically eject ejection seat 106, if the data collected from occupant 110 indicates occupant 110 is incapacitated and/or a catastrophic event is imminent. In various embodiments, smart deployment system 150 may provide audio and/or visual warnings to occupant 110 to indicate a health of aircraft 102, a detected danger, and/or whether deployment of the ejection system 100 is imminent. Smart deployment system 150 may further be configured to recognize a pilot override command, wherein smart deployment system 150 does not deploy ejection system 100 in response to receiving a pilot override command.

The smart deployment system 150 may include a controller 152. Controller 152 may include one or more logic devices such as one or more of a central processing unit (CPU), an accelerated processing unit (APU), a digital signal processor (DSP), a field programmable gate array (FPGA), an application specific integrated circuit (ASIC), or the like. In various embodiments, the controller 152 may further include any non-transitory memory known in the art. The memory may store instructions usable by the logic device(s) to perform operations and make determinations regarding the consciousness of occupant 110, the health of aircraft 102, and/or threats to aircraft 102.

In accordance with various embodiments, smart deployment system 150 may include a pilot health monitoring system 158. Pilot health monitoring system 158 may include a bio sensor assembly 160. Bio sensor assembly 160 may include non-invasive, light weight, sensors configured to monitor various physiological conditions of occupant 110. In various embodiments, bio sensor assembly 160 may include a smart watch 162, configured to be worn on the wrist of occupant 110. Smart watch 162 and/or other which may detect a blood pressure, heart rate, temperature, oxygen saturation, or other physiological condition of occupant 110. In various embodiments, bio sensor assembly 160 may include a bio-coherence electrode system 164 configured to monitor electrical brain activity of occupant 110. Bio-coherence electrode system 164 may include one or more sensors 165 configured to measure electrical activity in the brain of occupant 110. Sensors 165 may be operably coupled to the head and brain of occupant 110. In various embodiments, sensors 165 may be located on a skull cap 120 worn by occupant 110.

In various embodiments, bio sensor assembly 160 may include eye movement and/or facial recognition sensors 166. Sensors 166 may include camera(s), light detector(s), infrared detector(s), or any other sensor capable of detecting image data corresponding to any wavelength of light. Sensors 166 may be designed to detect eye movement and/or image data corresponding to a biometric feature of occupant 110. Sensors 166 may be located on canopy 112, on a helmet visor worn by occupant 110, or at any other location where the eyes and face of occupant 110 may be monitored. In various embodiments, pilot health monitoring system 158 may include an electrocardiogram (ECG) electrode system 168 configured to monitor heart activity of occupant 110. ECG electrode system 168 may include one or more sensors 169 configured to measure heart activity of occupant 110. Sensors 169 may be operably coupled to the chest and heart of occupant 110. In various embodiments, sensors 169 may be located on a chest strap 170 worn by occupant 110. Bio sensor assembly 160 may also include smart clothing or other non-invasive, wearable bio monitoring devices.

Pilot health monitoring system 158 may further include a sensor processing unit 174 configured to receive the bio data signals 172 from bio sensor assembly 160 (e.g. from smart watch 162, bio-coherence electrode system 164, eye movement and/or facial recognition sensors 166, and/or ECG electrode system 168). Bio data signals 172 may be sent via wired or wireless communication. Sensor processing unit 174 may perform signal conditioning and run various algorithms to detect a state of consciousness of occupant 110. Sensor processing unit 174 may make determinations regarding the state of consciousness of occupant 110 based on one or more of an electroencephalogram (EEG) generated from data output by bio-coherence electrode system 164, a blood pressure (BP), temperature and/or oxygen content of occupant 110 generated from data output from smart watch 162, eye movement data output from eye movement sensors 166, and/or an ECG generated from data output from ECG electrode system 168. Sensor processing unit 174 may employ sensor fusion algorithms to combine data from the various sensors of bio sensor assembly 160 and determine the consciousness of occupant 110 in real-time. Sensor processing unit 174 may be configured to consider into such factors as a health profile of occupant 110, the mission (e.g., is occupant flying a combat mission, in a warzone, etc.) or other factors when analyzing bio data signals 172 and determining the consciousness of occupant 110. Pilot health signals 178 corresponding to the consciousness of occupant 110 are output by sensor processing unit 174. Controller 152 receives the pilot health signals 178 output from sensor processing unit 174.

In accordance with various embodiments, controller 152 may also receive aircraft health signals 180 from an aircraft health monitoring system 182. Controller 152 is configured to interpret aircraft health signals 180 and determine whether the health or trajectory of aircraft 102 indicates an impending danger. Aircraft health monitoring system 182 is configured to monitor various operating parameters of aircraft 102. For example, aircraft health monitoring system 182 may be configured to detect significant failures such as engine failure, damage to control surfaces of aircraft, etc. Aircraft health monitoring system 182 may collect and interpret data from aircraft management systems 184, fuel systems 186, engine systems 188, flight control systems 190, and/or aircraft trajectory systems 192. Aircraft health monitoring system 182 may monitor the trajectory parameters of aircraft 102 such as altitude, descent rate, gravitation force applied occupant (e.g., Gx, Gy, and Gz), etc. Aircraft health monitoring system 182 may also communicate with an on-board global positioning system (GPS) to monitor the position of aircraft 102. In various embodiments, smart deployment system 150 may include an aircraft-monitoring-system-controller interface configured to collect desired data from aircraft health monitoring system 182 (i.e., data which may be used to determine a health and/or presence of impending danger) and translate the desired data to a form readable by controller 152.

Figure 4:
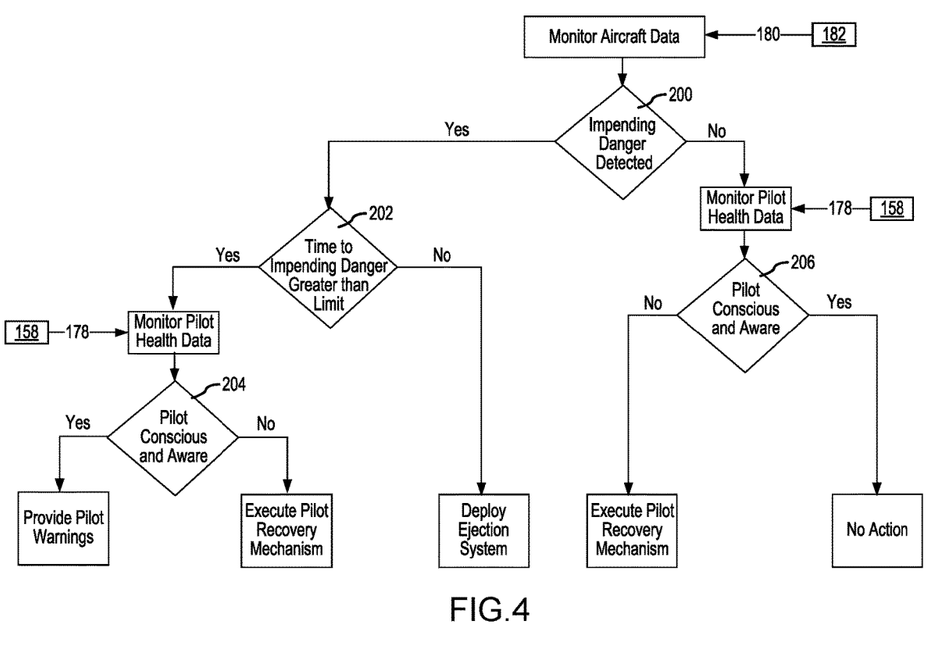
FIG. 4 illustrates a decision flowchart for a controller of a smart deployment system, in accordance with various embodiments.

Controller 152 receives pilot health signals 178 and aircraft health signals 180 and performs various decision making activities based on signals 178 and 180. FIG. 4 illustrates a flow diagram for decisions, which may be made by controller 152 based on pilot health signals 178 and aircraft health signals 180. With combined reference to FIG. 3 and FIG. 4, in accordance with various embodiments, controller 152 may continually monitor a health of aircraft 102 using aircraft health signals 180. Controller 152 may also continually monitor a health of occupant 110 based using pilot health signals 178. At decision 200, controller 152 may determine if aircraft health signals 180 indicate an impending danger. Stated differently, controller 152 may detect whether there is an impending danger based on one or more aircraft health signals 180.

If controller 152 determines an impending danger is being detected, controller 152 estimates a time until the impending danger occurs and determines if the estimated time is greater than or less than a predetermined time threshold (decision 202). If controller 152 determines the estimated time is less than the predetermined time threshold, controller 152 sends an ejection command 300 to ejection system 100. Ejection command 300 may be configured to initiate a deployment sequence for ejection system 100 and expel ejection seat 106 from cockpit 104.

If controller 152 determines the estimated time is greater than or equal to the predetermined time threshold, then controller 152 determines whether occupant 110 is conscious and/or aware (decision 204). Controller 152 is configured to make decision 204 (i.e., to determine whether the pilot is conscious and aware) using pilot health signals 178 from pilot health monitoring system 158. If controller 152 determines, based on pilot health signals 178, that occupant 110 is conscious and/or aware, controller 152 may send commands 302 to a pilot warning system 304. Pilot warning system 304 may output audio alerts 306 and/or visual alerts 308, in response to receiving commands 302. Alerts 306, 308 are configured to convey to occupant 110 that a danger has been detected. In this regard, because occupant 110 is conscious and/or aware, controller 152 can convey the health status of aircraft 102 and/or the impending danger to occupant 110 and because the estimated time is greater than the threshold time, occupant 110 may be able to take action to avoid the danger. For example, a damage incurred by aircraft 102 may be causing fuel to leak from the aircraft, and the fuel quantity and rate at which fuel volume is decreasing may be conveyed to occupant 110 via warning system 304. Warning system 304 may be configured to convey any information that may be useful to occupant 110. For example, in the above scenario, warning system 304 may convey a distance that can be covered by aircraft 102 based on the fuel data and/or warning system 304 may use GPS information and provide suggestions as to where occupant 110 should land aircraft 102 and/or when occupant 110 should begin returning towards base so that occupant 110 can land aircraft 102 or eject from aircraft 102 in safe airspace. In this regard, smart deployment system 150 is able to determine that there is adequate time before a catastrophic failure and that the occupant is conscious and aware, and then, using the warning system 304, smart deployment system 150 allows occupant 110 to perform tasks based on his/her judgment of the situation.

If controller 152 determines that the estimated time to impending danger is greater than or equal to the threshold time and, based on pilot health signals 178, that occupant 110 is not conscious and/or not aware, controller sends commands 310 to one or more pilot recovery mechanisms 312. In this regard, temporary incapacitation of occupant 110 will not cause an ejection, unless it is in combination with, for example, a descent rate and an altitude that indicate an aircraft crash is imminent.

Controller 152 may be configured to determine which pilot recovery mechanisms 312 are to be employed based on, for example, aircraft health signals 180 and/or the difference between the estimated time until the impending danger and the threshold time. Controller 152 may be configured to deduce (i.e., determine) the potential, or likely, causes of occupant loss of conciseness and make pilot recovery mechanism 312 decisions based on the determined likely cause of incapacitation. For example, fatigue caused due to continued operation in extreme high temperatures can be counteracted by a recovery mechanism that includes blowing cool air on the pilot. Or if a pilot has lost consciousness in an aircraft that is at a high altitude, a recovery mechanism of auditory provocations may be initiated and whether occupant 110 has a response to the auditory provocations may be monitored by controller 152 using, for example, audio evoked potential algorithms. Multiple recovery mechanisms can be triggered simultaneously. For example, controller 152 may order one or more of blowing of cool air, providing auditory stimulus, and/or vibrations to the pilot's chair or steering wheel at any one time. In various embodiments, if mild recovery methods (e.g., blowing cool air, auditory stimulus, flashing lights, vibrations, etc.), do not invoke consciousness in occupant 110, and the situation is progressing towards catastrophe (e.g., if the estimated time to impending danger is approaching the threshold time), a recovery mechanism including mild electrical shocks to occupant 110 may be attempted. Decisions of which recovery mechanism(s) is/are to be initiated may be determined by controller 152 based on pilot health signals 178 and aircraft health signals 180.

In various embodiments, controller 152 may also send commands 310 to one or more pilot recovery mechanisms 312, if, based on aircraft health signals 180, controller 152 determines no impending danger is being detected (decision 200) and, based on pilot health signals 178 from pilot health monitoring system 158, that occupant 110 is not consciousness and/or not aware (decision 206).

Finally, if, based on pilot health signals 178, controller 152 determines no impending danger is being detected (decision 200) and that occupant 110 is conscious and/or aware (decision 206), controller 152 takes no action.

In various embodiments, smart deployment system 150 includes a pilot override mechanism 320. For example, in certain situation, occupant 110 may choose to not be ejected from cockpit 104, and thus may choose to remain in aircraft 102. For example, occupant may choose to attempt to land the aircraft and/or guide the aircraft away from people on the ground regardless of the imminent danger to the pilot and the aircraft. In this regard, occupant 110 may cause pilot override mechanism 320 to send an override signal 322 to controller 152. Override signal 322 is configured to bypass or otherwise disable controller 152 from sending ejection command 300 to ejection system 100. The override signal 322 may be accomplished by pressing a button, or in response to controller receiving a voice command from occupant 110. Override signal 322 is configured to prevent smart deployment system 150 from sending ejection command 300 and initiating deployment ejection system 100 while still allowing ejection system 100 still to be deployed manually, for example, via actuation of handle 114.

In accordance with various embodiments, smart deployment system 150 may include various redundancies and/or dissimilar and failsafe architectures to decrease a probability of failure conditions. For example, it is desirable to avoid a failure condition where ejection occurs when it is not required and a failure condition where ejection functionality is not operative when pilot wants to eject manually. In this regard, smart deployment system 150 may be designed to be qualified at the highest and/or most stringent design assurance levels (e.g., design assurance level A). Bio sensor assembly 160 may include a dual, redundant sensors. In various embodiments, one or more of the sensor(s) may be of dissimilar type to avoid common mode failures. Aircraft health monitoring system 182, sensor processing unit 174, and controller 152 may each have a dual redundant architectures. The critical algorithms of each of the aircraft health monitoring system 182, sensor processing unit 174, and/or controller 152 may be dissimilar. The sensors, electrical components, memory, etc. of smart deployment system 150 may have robust built-in test coverage. The pilot override mechanism 320 that overrides and disables smart deployment system 150 from sending ejection command 300 may be a parallel and isolated mechanism.

Benefits and other advantages have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, and any elements that may cause any benefit or advantage to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods, and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A smart deployment system for an ejection system, the smart deployment system comprising:
    a pilot health monitoring system including a plurality of sensors configured to detect a plurality of physiological conditions;
    an aircraft health monitoring system configured to monitor one or more parameters of an aircraft;
    a first pilot recovery mechanism corresponding to fatigue;
    a second pilot recovery mechanism corresponding to altitude;
    a controller operationally coupled to the pilot health monitoring system and the aircraft health monitoring system; and
    a tangible, non-transitory memory configured to communicate with the controller, the tangible, non-transitory memory having instructions stored thereon that, in response to execution by the controller, cause the controller to perform operations comprising:
        receiving, by the controller, a pilot health signal from the pilot health monitoring system,
        receiving, by the controller, an aircraft health signal from the aircraft health monitoring system,
        determining, by the controller, at least one of a consciousness or an awareness of an occupant based on the pilot health signal,
    determining, by the controller, a likely cause of at least one of the consciousness or the unawareness of the occupant,
    determining, by the controller, whether to employ at least one of the first pilot recovery mechanism or the second pilot recovery mechanism based on the likely cause of the consciousness or the unawareness of the occupant, and
        determining, by the controller, whether to initiate an ejection sequence based on the at least one of the consciousness or the awareness of the occupant and the aircraft health signal.

2. The smart deployment system of claim 1, wherein the operations further comprise detecting, by the controller, if there is an impending danger to the aircraft based on the aircraft health signal.

3. The smart deployment system of claim 2, wherein the operations further comprise:
    calculating, by the controller, an estimated time for when the impending danger will occur, in response to the controller detecting the impending danger to the aircraft; and
    comparing, by the controller, the estimated time for when the impending danger to the aircraft will occur to a predetermined threshold time.

4. The smart deployment system of claim 3, wherein the operations further comprise determining, by the controller, if the estimated time for when the impending danger will occur is less than the predetermined threshold time.

5. The smart deployment system of claim 4, wherein the controller is configured to send an ejection command configured to initiate the ejection sequence in response to the controller determining that the estimated time for when the impending danger will occur is less than the predetermined threshold time.

6. The smart deployment system of claim 5, wherein the controller is configured to recognize a pilot override signal, the pilot override signal being configured to prevent the controller from sending the ejection command to the ejection system.

7. The smart deployment system of claim 4, wherein the controller is configured to send a command to a pilot warning system in response to the controller determining that the occupant is at least one of conscious or aware and the controller determining that the estimated time for when the impending danger will occur is greater than or equal to the predetermined threshold time.

8. The smart deployment system of claim 7, wherein the pilot warning system is configured to output at least one of an audio alert or a visual alert in response to receiving the command from the controller.

9. The smart deployment system of claim 4, wherein the controller is configured to send a command to a pilot recovery mechanism in response to the controller determining that the occupant is at least one of unconscious or unaware and the controller determining that the estimated time for when the impending danger will occur is greater than or equal to the predetermined threshold time.

10. The smart deployment system of claim 9, wherein the pilot recovery mechanism is configured to output at least one of an auditory stimulus, a flow of cool air, a flash of light, a vibration, or an electric shock in response to receiving the command from the controller.

11. The smart deployment system of claim 1, wherein the plurality of sensors include a first sensor configured to measure electrical brain activity, a second sensor configured to detect eye movement, and a third sensor configured to detect at least one of a heart rate, a blood pressure, or an oxygen level.

12. A method for controlling deployment of an ejection system for an aircraft, the method comprising:
receiving, by a controller, a pilot health signal from a pilot health monitoring system;
receiving, by the controller, an aircraft health signal from an aircraft health monitoring system;
determining, by the controller, at least one of a consciousness or an awareness of an occupant based on the pilot health signal;
determining, by the controller, a likely cause of at least one of the consciousness or the unawareness of the occupant;
determining, by the controller, whether to employ at least one of a first pilot recovery mechanism corresponding to fatigue or a second pilot recovery mechanism corresponding to altitude based on the likely cause of the consciousness or the unawareness of the occupant; and
determining, by the controller, whether to initiate an ejection sequence based on the at least one of the consciousness or the awareness of the occupant and the aircraft health signal.

13. The method of claim 12, further comprising determining, by the controller, whether or not there is an impending danger to the aircraft based on the aircraft health signal.

14. The method of claim 13, further comprising:
calculating, by the controller, an estimated time for when the impending danger to the aircraft will occur, in response to the controller detecting the impending danger to the aircraft; and
comparing, by the controller, the estimated time for when the impending danger to the aircraft will occur to a predetermined threshold time.

15. The method of claim 14, further comprising sending, by the controller, an ejection command to the ejection system, in response to the controller determining that the estimated time for when the impending danger will occur is less than the predetermined threshold time, wherein the ejection command is configured to initiate the ejection sequence.

16. The method of claim 14, further comprising sending, by the controller a command to a pilot warning system, in response to the controller determining that the occupant is at least one of conscious or aware and the controller determining that the estimated time for when the impending danger will occur is greater than or equal to the predetermined threshold time.

17. The method of claim 14, further comprising sending, by the controller, a command to a pilot recovery mechanism, in response to the controller determining that the occupant is at least one of unconscious or unaware and the controller determining that the estimated time for when the impending danger will occur is greater than or equal to the predetermined threshold time.

18. The method of claim 17, wherein the pilot recovery mechanism is configured to output at least one of an auditory stimulus, a flow of cool air, a flash of light, a vibration, or an electric shock in response to receiving the command from the controller.

19. An ejection system, comprising:
an ejection seat; and
a smart deployment system configured to initiate a deployment of the ejection seat, the smart deployment system comprising:
a pilot health monitoring system including a plurality of sensors configured to detect a plurality of physiological conditions;
a first pilot recovery mechanism corresponding to fatigue;
a second pilot recovery mechanism corresponding to altitude; and
a controller configured to make a pilot recovery mechanism decision to employ at least one of the first pilot recovery mechanism or the second pilot recovery mechanism based on determining the likely cause of at least one of the plurality of physiological conditions, and configured to make a ejection system decision based on a pilot health signal received from the pilot health monitoring system and an aircraft health signal output from an aircraft health monitoring system.

20. The ejection system of claim 19, wherein the controller is configured to determine whether an occupant of the ejection seat is at least one of conscious or aware based on the pilot health signal, and wherein the controller is configured to determine if there is an imminent danger based on the aircraft health signal output from the aircraft health monitoring system.

* * * * *